(12) United States Patent
Ryu et al.

(10) Patent No.: US 7,917,216 B1
(45) Date of Patent: Mar. 29, 2011

(54) MULTI-SITE PACING FOR ATRIAL TACHYARRHYTHMIAS

(75) Inventors: Kyungmoo Ryu, Palmdale, CA (US); Jong Gill, Valencia, CA (US); Xiaoyi Min, Thousand Oaks, CA (US); Annapurna Karicherla, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1004 days.

(21) Appl. No.: 11/458,649

(22) Filed: Jul. 19, 2006

(51) Int. Cl.
*A61N 1/18* (2006.01)

(52) U.S. Cl. .......... 607/14; 607/4; 607/5; 607/9; 607/15

(58) Field of Classification Search .................. 607/4, 5, 607/9
See application file for complete search history.

(56) References Cited

U.S. PATENT DOCUMENTS

| | | | |
|---|---|---|---|
| 4,872,459 A * | 10/1989 | Pless et al. ................ | 607/15 |
| 5,144,947 A * | 9/1992 | Wilson ........................ | 607/15 |
| 5,181,511 A | 1/1993 | Nickolls et al. | |
| 5,562,708 A | 10/1996 | Combs et al. | |
| 5,674,251 A | 10/1997 | Combs et al. | |
| 5,800,465 A | 9/1998 | Thompson et al. | |
| 5,855,592 A | 1/1999 | McGee et al. | |
| 6,473,645 B1 | 10/2002 | Levine | |
| 6,484,057 B2 * | 11/2002 | Ideker et al. ................ | 607/14 |
| 6,731,982 B1 * | 5/2004 | Kroll et al. ................ | 607/14 |
| 6,754,531 B1 * | 6/2004 | Kroll et al. ................ | 607/14 |
| 6,766,196 B1 * | 7/2004 | Kroll et al. ................ | 607/14 |
| 6,795,731 B1 * | 9/2004 | Kroll et al. ................ | 607/14 |
| 6,829,506 B2 * | 12/2004 | Pastore et al. ............... | 607/9 |
| 6,885,890 B2 | 4/2005 | Spinelli et al. | |
| 7,146,214 B2 * | 12/2006 | Struble ........................ | 607/14 |
| 2001/0005790 A1 * | 6/2001 | Ripart .......................... | 607/14 |
| 2002/0151934 A1 | 10/2002 | Levine | |
| 2002/0151935 A1 | 10/2002 | Levine | |
| 2002/0161410 A1 | 10/2002 | Kramer et al. | |
| 2002/0193834 A1 | 12/2002 | Levine | |
| 2002/0193836 A1 | 12/2002 | Schmidt | |
| 2003/0120315 A1 | 6/2003 | Spinelli et al. | |
| 2003/0120316 A1 | 6/2003 | Spinelli et al. | |
| 2004/0049236 A1 | 3/2004 | Kramer et al. | |

(Continued)

FOREIGN PATENT DOCUMENTS

| WO | WO9847564 | 10/1998 |
|---|---|---|
| WO | 02087501 A2 | 11/2002 |
| WO | 02087501 A3 | 11/2002 |

(Continued)

OTHER PUBLICATIONS

Ryu, Kyungmoo, Comparative effects of single- and linear triple-site rapid bipolar pacing on atrial activation in canine models, Am J Physiol Heart Circ Physiol 289; H1-H11 (2005) (www.ajpheart.org).

*Primary Examiner* — Niketa I Patel
*Assistant Examiner* — Joseph Stoklosa

(57) ABSTRACT

Tachyarrhythmia is treated by applying anti-tachycardia pacing through at least one multi-site electrode set located on, in or around the heart. The electrode set is arranged and located such that an electrical activation pattern having a wave-front between substantially flat and concave is generated through a reentrant circuit associated with the tachyarrhythmia. The electrode set may be one of a plurality of predefined, multi-site electrode sets located on, in or around the atria. Alternatively, the electrode set may be formed using at least two selectable electrodes located on, in or around the atria.

12 Claims, 8 Drawing Sheets

U.S. PATENT DOCUMENTS

2004/0088014 A1  5/2004  Burnes
2005/0090869 A1  4/2005  Sun et al.
2005/0090870 A1  4/2005  Hine et al.

FOREIGN PATENT DOCUMENTS

WO   WO03053510 A2   7/2003
WO   WO03053510 A3   7/2003
WO   WO2004041357 A1   5/2004

* cited by examiner

MULTI-SITE PACING FOR ATRIAL TACHYARRHYTHMIAS

FIELD OF THE INVENTION

The invention relates generally to cardiac devices and more particularly to implantable devices having multi-site pacing capability for preventing and terminating atrial tachyarrhythmias.

BACKGROUND

The physiological mechanisms of atrial tachyarrhythmias are often single, stable, reentrant circuit of very short cycle duration, which drives the atria, producing arrhythmic conduction. A reentrant circuit is typically a physical and electrical feedback loop composed of cardiac cells that repeatedly cycle electrical impulses in a tight circle and spin off abnormal impulses that propagate over the heart atrial tachycardia. Such a problem feedback loop or "driver," may be originated by a "trigger," such as an abnormally occurring spontaneous depolarization of cell membrane in the myocardial tissue. Drivers are typically very regular, and each trigger can initiate many variations of these reentrant pathways. Resulting reentrant circuits can be large or small, i.e., a macro reentrant circuit, or instead, a small micro reentrant circuit, e.g., less then 1 mm in diameter. These small drivers can even mimic a trigger, although they are really small reentrant circuits.

A typical cycle duration for such a reentrant circuit is on the order of 100-200 milliseconds (ms). This is the equivalent of 600 beats per minute at a 100 ms cycle duration. If there is no such trigger and no resulting reentrant circuit, then tachyarrhythmia conduction will not be there, i.e., the electrical conduction will be normal intrinsic conduction from an intrinsic rhythm (e.g., normal sinus rhythm).

Reentrant circuits can be further understood in terms of cellular action potentials continually propagating around the reentrant circuit at a rate considerably faster than the heart's intrinsic rate, provided that the reentrant wave front, i.e. the head of the propagation wave front, moves slowly enough that tissue ahead recovers excitability, i.e., slowly enough that a tail or end of the propagation wave front can form. The spatial extent of unexcitable tissue in this circuit is termed the reentrant wavelength, and is approximated by the product of the head's velocity and the action potential duration. As long as the wavelength is less than the circuit's perimeter, i.e. the reentrant path length, the head and tail remain separated by an "excitable gap" of tissue waiting to be stimulated. Termination of anatomic reentry requires elimination of the excitable gap, which can be achieved by appropriate pacing. An appropriately timed pacing pulse will initiate action potentials that propagate in both directions, colliding with the head and "blocking in" the tail.

In more simplified terms, the reentrant circuit can be thought of as a conduction wave front propagating along a tissue mass of somewhat circular geometry. This circular conduction will consist of a portion of refractory tissue and a portion of excitable tissue. To terminate the circuit, a pacing stimulus should be provided at the time and location when the tissue just comes out of refractoriness. If this occurs, the paced stimulation wave front proceeds toward the advancing wave front of the circuit, colliding with the wave front and interrupting the circuit. If the pacing stimulus arrives too soon it will be ineffective because the tissue will still be in refractoriness. If the stimulus arrives too late, it will generate wave fronts both towards the advancing wave front and towards the tail of the circuit. Although one pacing-generated wave front will collide with the advancing wave front of the reentrant circuit and will halt is progress, the latter pacing-generated wave front will act to sustain the reentrant circuit.

Anti-tachycardia pacing (ATP) is a standard treatment option to terminate most reentrant tachycardias. Overdrive pacing techniques to interrupt or to prevent tachycardias virtually always are performed by pacing from a single-site. Studies, however, have demonstrated that rapid pacing from a single-site can be proarrhythmic due to production of conduction abnormalities which may contribute to the onset and maintenance of atrial tachyarrhythmias.

Recent studies in normal and abnormal atria have demonstrated that linear triple site rapid bipolar pacing, compared with single site bipolar rapid pacing, produces 1) more uniform linear activation wave fronts; 2) shorter right atrial and bi-atrial activation time and faster mean epicardial speed; and 3) velocity vectors with a more uniform magnitude and direction. It has been suggested that a concave (i.e., curving inward) wave front creates more rapid depolarization in front of the advancing wave front compared with a flat wave front pattern. This is because the local excitatory current of the concave wave front pattern is larger than that of the flat wave front pattern. When the wave front is convex (i.e., curving outward), the wave front travels more slowly than the flat wave front, because the local excitatory current is distributed over a larger area in front of the wave front than the flat wave front. See *Comparative Effects of Single- and Linear Triple-site Rapid Bipolar Pacing on Atrial Activation in Canine Models*, Ryu et al., Am J Physiol Heart Circ Physiol, Vol. 289.

SUMMARY

Briefly, and in general terms, the invention is directed to the treatment of tachyarrhythmia by application of anti-tachycardia pacing through at least one multi-site electrode set located on, in or around the heart. The electrode set is arranged and located such that an electrical activation pattern having a wave-front between substantially flat and concave is generated through a reentrant circuit associated with the tachyarrhythmia. The electrode set may be one of a plurality of predefined, multi-site electrode sets located on, in or around the atria. Alternatively, the electrode set may be formed using at least two selectable electrodes located on, in or around the atria.

These and other aspects and advantages of the invention will become apparent from the following detailed description and the accompanying drawings which illustrate by way of example the features of the invention.

DETAILED DESCRIPTION

Figure 1A:
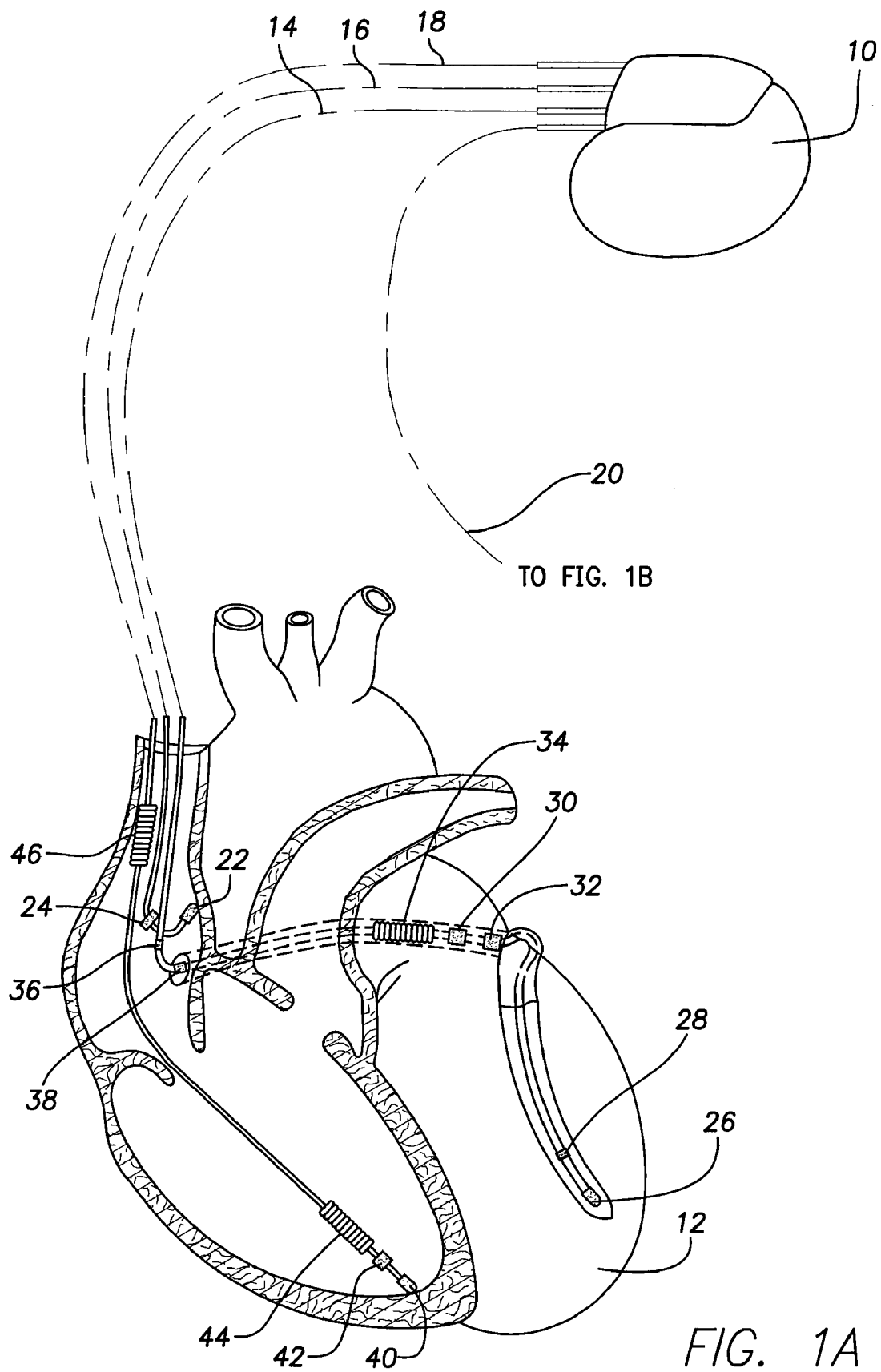
FIGS. 1A and 1B are schematic representations of an implantable device in relation to a human heart, viewed from the anterior (FIG. 1A) and the posterior (FIG. 1B)

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

This disclosure described systems and methods for delivering anti-tachycardia pacing (ATP) to treat atrial tachyarrhythmias. The system analyzes input from multiple electrodes on, in or near the left and right atria for the presence of one or more regularly cycling reentrant circuits. If cycling reentrant circuits are present, the system determines the approximate location of the one or more reentrant circuits or their associated drivers and selects one or more predefined multi-electrode sets, or alternatively forms a multi-site electrode set using a plurality of the atrial electrodes. The multi-site electrode sets are selected or formed such that when electrically stimulated, they create a substantially linear to concave electrical activation wave front through the cardiac tissue toward the one or more reentrant circuits or drivers.

The multiple electrodes may be placed relative to the right and left atria on the epicardial surface, the endocardial surface or a combination of the two surfaces. Electrodes may also be placed relative to the right and left atria implanted within myocardium. The system uses the multiple electrodes to sense abnormal activation within one or both of the atria and the abnormal electrical pathways in cardiac tissue that drive atrial tachyarrhythmias. At each electrode, the system senses signals associated with any reentrant circuits. Based on the timing and/or magnitude of sensed signals, the system selects one or more predefined multi-site electrode sets, or individual electrodes to form one or more multi-site electrode sets, that produce a desirable activation wave front, i.e., a substantially linear to concave wave front, directed toward a reentrant circuit or driver.

The probability of ATP succeeding in terminating atrial tachyarrhythmia is related to the ability of the substantially linear to concave activation wave front to arrive at the location of a targeted reentrant circuit or driver in such a manner that the reentrant circuit is modified or interrupted. Factors influencing this process may include the distance of the multi-site electrode sets from the reentrant circuit, the pacing stimulus energy, and the timing of the pacing stimuli relative to the conduction velocities and refractory periods of the myocardium. Thus, there are several parameters that can be optimized to make ATP suitable for effectively terminating atrial tachyarrhythmia. The exemplary system achieves the ability to apply optimal ATP through one or more multi-site electrode sets located relative the left and right atria.

Figure 1B:
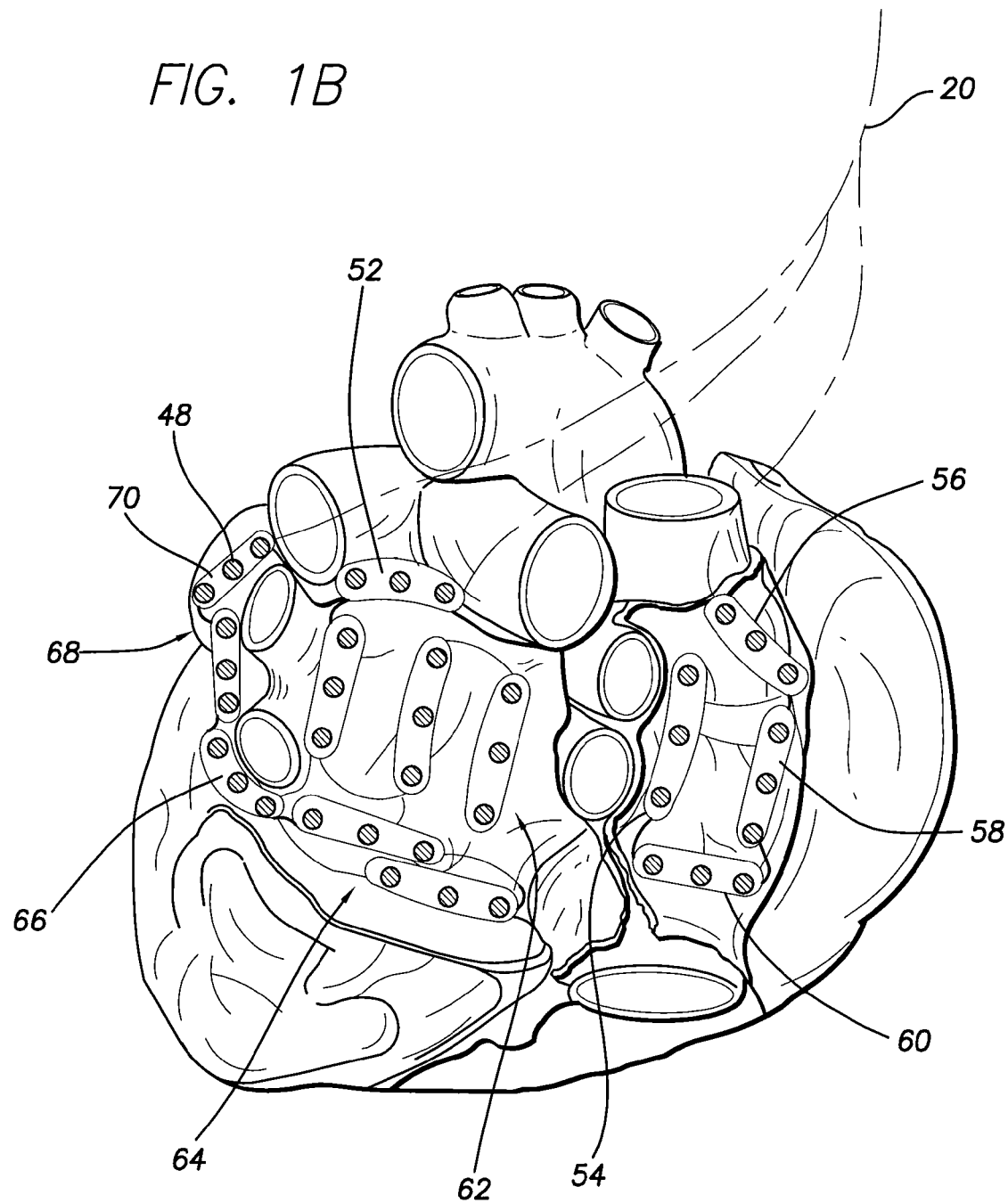

Referring now to the drawings and particularly to FIGS. 1A and 1B, there is shown a stimulation device 10 in electrical communication with a patient's heart 12 by way of four leads 14, 16, 18, and 20 for delivering one or more of multi-chamber stimulation, anti-tachycardia pacing and shock therapy. The stimulation device 10, which may also be referred to as a cardiac rhythm management device or an implantable medical device, may function as one or more of a pacing apparatus, cardioverter/defibrillator or cardiac resynchronization device.

With reference to FIG. 1A, to sense atrial cardiac signals and to provide right atrial chamber stimulation therapy, the stimulation device 10 is coupled to an implantable right atrial lead 16, typically having an atrial tip electrode 22 and an atrial ring electrode 24, which typically is implanted in the patient's right atrial appendage.

To sense left atrial and ventricular cardiac signals and to provide left chamber pacing therapy, the stimulation device 10 is coupled to a "coronary sinus" lead 14 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 14 is designed to receive atrial and ventricular cardiac signals and to deliver left ventricular pacing therapy using a left ventricular (LV) tip electrode 26 and a LV ring electrode 28. Left atrial pacing therapy uses, for example, first and second left atrial (LA) ring electrodes 30 and 32. Shocking therapy can be performed using at least a left atrial (LA) coil electrode 34. For a description of an exemplary coronary sinus lead, see U.S. Pre-Grant Publication No. 20030050681, "A Self-Anchoring Coronary Sinus Lead" (Pianca et al.), and U.S. Pat. No. 5,466,254 to Helland, entitled, "Coronary Sinus Lead with Atrial Sensing Capability," which patent documents are incorporated herein by reference. Coronary sinus lead 14 may also include a pair of right atrial (RA) ring electrodes 36 and 38, which may be used to provide right atrial chamber pacing therapy.

The stimulation device 10 is also shown in electrical communication with the patient's heart 12 by way of an implantable right ventricular lead 18, typically having an right ventricular (RV) tip electrode 40, an RV ring electrode 42, an RV coil electrode 44, and a superior vena cava (SVC) coil electrode 46 (also known as a right atrial (RA) coil electrode). Typically, the right ventricular lead 18 is transvenously inserted into the heart 12 so as to place the right ventricular tip electrode 40 in the right ventricular apex so that the RV coil electrode 44 will be positioned in the right ventricle and the SVC coil electrode 46 will be positioned in the superior vena cava. Accordingly, the right ventricular lead 18 is capable of receiving cardiac signals, and delivering stimulation in the form of pacing and shock therapy to the right ventricle.

With reference to FIG. 1B, an implantable atrial lead system 20 couples the stimulation device 10 to multiple electrodes 48 placed epicardially relative to the left atrium and the right atrium. Although shown schematically as one lead 20, the atrial lead system may be formed of two or more separate leads each coupling the stimulation device 10 to the electrodes 48. The electrodes 48 may have any of several configurations. For example, they may be ring electrodes located on a tubular portion of the lead body or hemispherical electrodes carried by a patch. The electrodes 48 are closely spaced such that the stimulation device 10 may operate the electrodes as functional pairs, i.e., bipolar mode, or individually, i.e., unipolar mode. During unipolar operation, the reference electrode may be the device case or a coil electrode on an endocardial lead, such as the right atrial SVC coil 46 (FIG. 1A).

The multiple electrodes 48 are typically placed in locations suitable for both sensing reentrant circuits and applying ATP to terminate tachyarrhythmia conduction. For example, one or more electrodes 48 may be placed in or around: the area of Bachmann's Bundle 52, the intercaval region 54, the high right atrium 56, the mid-right atrial free wall 58, the low right atrial free wall 60, the pulmonary veins region 62, the posterior/inferior left atrium region 64, the anterior left atrial free wall 66 and the junction 68 of the left atrial appendage and the left pulmonary veins.

In order to place the electrodes 48 epicardially in the above-mentioned locations, the pericardial sac may be entered via a sub-xiphoid approach and the electrodes mapped to sites where reentrant circuits or drivers for sustaining atrial tachyarrhythmia likely originate. In one scenario, an electroanatomical mapping system (e.g., ENSITE, St. Jude Medical, Inc., St. Paul, Minn.) may be used for an accurate placement of the electrodes 48 on the epicardial surfaces. Placing the electrodes 48 epicardially on the left and right atria does not preclude having electrodes located on the endocardial surfaces of the atria or inside the atria or pulmonary veins.

In one configuration, groups of the atrial electrodes 48 form predefined, multi-site electrode sets 70. For example, the atrial electrodes 48 may be grouped together in sets of three to provide a number of triple-site electrode sets. In other configurations, the atrial electrodes 48 may have no predefined association with other electrodes and thus may be independently selected to form multi-site electrode sets. In either case, individual electrodes 48 or groups of electrodes 70, i.e., predefined electrode sets, may be independently connected to the device 10 through separate conductors or daisy chained together. In a daisy-chain configuration, the lead may include an ASIC/multiplexer that provides for individualized selection of electrodes 48 or electrode sets 70 for sensing and stimulation.

Figure 2:
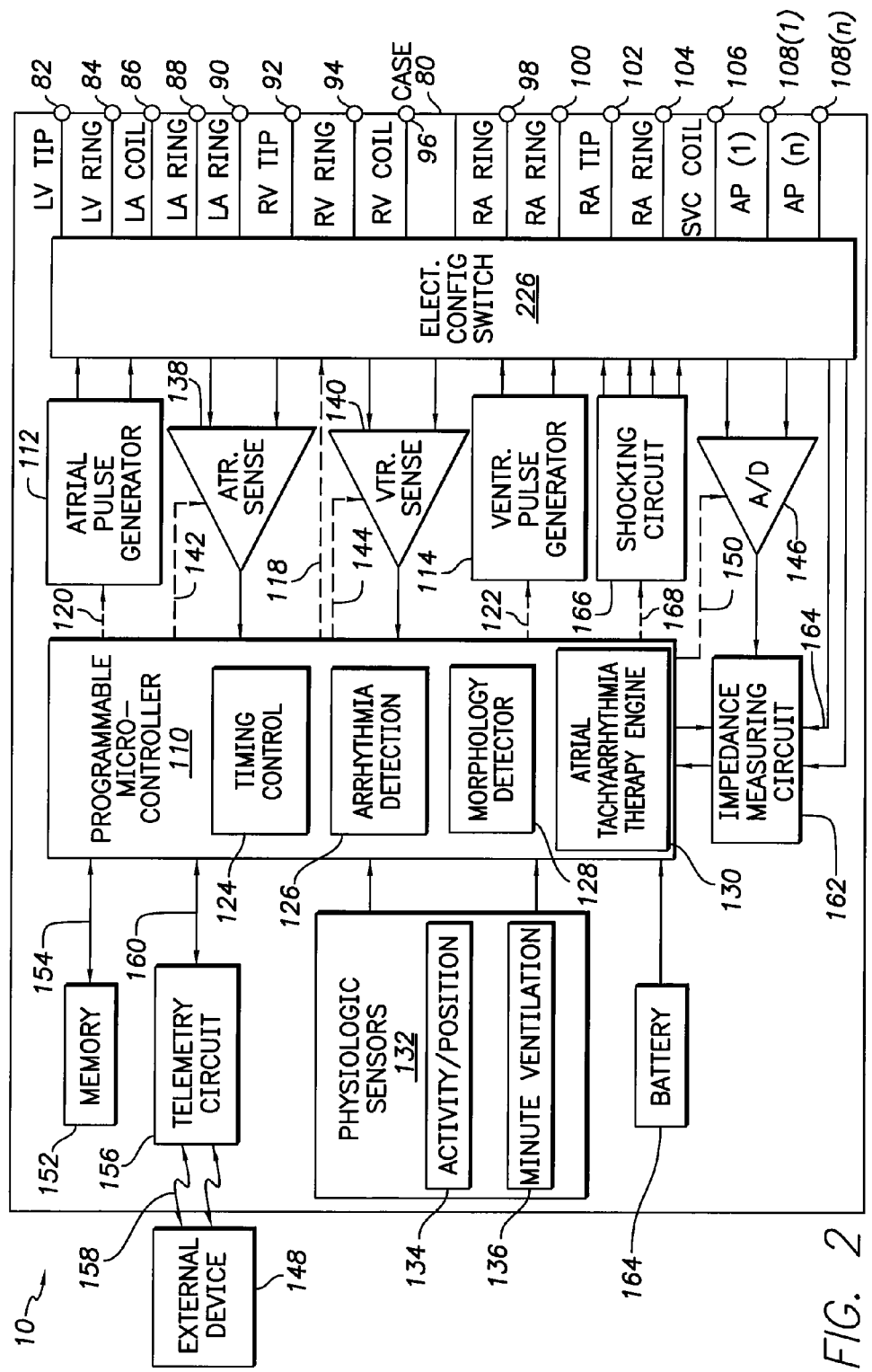
FIG. 2 is a functional block diagram of the implantable stimulation device of FIGS. 1A and 1B.

FIG. 2 shows an exemplary block diagram depicting various components of the exemplary stimulation device 10. The components are typically contained in a case 80, which is often referred to as the "can", "housing", "encasing", or "case electrode", and may be programmably selected to act as the return electrode for unipolar operational modes. The case 200 may further be used as a return electrode alone or in combination with one or more of the coil electrodes 34, 44, 46 for stimulating purposes. The case 80 further includes a connector (not shown) having a plurality of terminals (82, 84, 86, 88, 90, 92, 94, 96, 98, 100, 102, 104, 106 and 108—shown schematically with the names of the electrodes to which they are connected shown next to the terminals). Left-heart terminals include: a left ventricular tip terminal (LV TIP) 82 for the left ventricular tip electrode 26, a left ventricular ring terminal (LV RING) 84 for the left ventricular ring electrode 28, a left atrial shocking terminal (LA COIL) 86 for the left atrial coil electrode 34, a left atrial ring terminal (LA RING) 88 for the left atrial ring electrode 30 and a left atrial ring terminal (LA RING) 90 for the left atrial ring electrode 32;

Right-heart terminals include: a right ventricular tip terminal (RV TIP) 92 for the right ventricular tip electrode 40, a right ventricular ring terminal (RV RING) 94 for the right ventricular ring electrode 42, a right ventricular shocking terminal (RV COIL) 96 for the RV coil electrode 44, a right atrial ring terminal (RA RING) 98 for the atrial ring electrode 36, a right atrial ring terminal (RA RING) 100 for the right atrial ring electrode 38, a right atrial tip terminal (RA TIP) 102 for the atrial tip electrode 22, a right atrial ring terminal (RA RING) 104 for the atrial ring electrode 24 and a SVC shocking terminal (SVC COIL) 106 for the right atrial SVC coil electrode 46.

Regarding the epicardial atrial electrodes 48, a plurality of atrial pacing terminals (AP1-APn) 108 are provided for independent connection with individual electrodes 48 or electrode sets 70. In the case of an ASCI/multiplex lead configuration, one pacing terminal 108 may be sufficient.

An exemplary stimulation device 10 may include a programmable microcontroller 110 that controls various operations of the stimulation device, including cardiovascular monitoring, hemodynamic monitoring, and cardiovascular stimulation therapy. Microcontroller 110 includes a microprocessor (or equivalent control circuitry), RAM and/or ROM memory, logic and timing circuitry, state machine circuitry, and I/O circuitry.

The exemplary stimulation device 10 may further include an atrial pulse generator 112 and a ventricular pulse generator 114 that generate pacing stimulation pulses for delivery by the right atrial lead 16, the coronary sinus lead 14, the right ventricular lead 18 and/or the atrial lead system 20 via an electrode configuration switch 116. The electrode configuration switch 116 may include multiple switches for connecting the desired electrodes to the appropriate I/O circuits, thereby providing complete electrode programmability. Accordingly, switch 216, in response to a control signal 118 from the microcontroller 110, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 112 and 114 may include dedicated, independent pulse generators, multiplexed pulse generators, or shared pulse generators. The pulse generators 112 and 114 are controlled by the microcontroller 110 via appropriate control signals 120 and 122, respectively, to trigger or inhibit the stimulation pulses.

Microcontroller 110 is illustrated as including timing control circuitry 124 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 110 may also implement an arrhythmia detector 126, a morphology detector 128, and an atrial tachyarrhythmia therapy engine 130. The microcontroller 110 may process input from physiological sensors 132, such as accelerometers of an activity/position module 134, and a minute ventilation module 136 etc., The components 126, 128, 130 may be implemented in hardware as part of the microcontroller 110, or as software/firmware instructions programmed into an implementation of the stimulation device 10 and executed on the microcontroller 110 during certain modes of operation. Although not shown, the microcontroller 110 may further include other dedicated circuitry and/or firmware/software components that assist in monitoring various conditions of the patient's heart and managing pacing therapies.

Atrial sensing circuits 138 and ventricular sensing circuits 140 may also be selectively coupled to the right atrial lead 16, coronary sinus lead 14, the right ventricular lead 18 and/or the atrial lead system 20 through the switch 116 to detect the presence of cardiac activity with respect to each of the four chambers of the heart. The sensing circuits 138 and 140 may include dedicated sense amplifiers, multiplexed amplifiers, or shared amplifiers. Switch 116 determines the "sensing polarity" of the cardiac signal by selectively closing the appropriate switches. In this way, the clinician may program the sensing polarity independent of the stimulation polarity.

Each sensing circuit 138 and 140 may employ one or more low power precision amplifiers with programmable gain and/or automatic gain control, bandpass filtering, and a threshold detection circuit to selectively sense the cardiac signal of interest. The automatic gain control enables the exemplary stimulation device 10 to sense low amplitude signal characteristics of atrial or ventricular fibrillation.

The outputs of the atrial and ventricular sensing circuits 138 and 140 are connected to the microcontroller 110 which, in turn, is able to trigger or inhibit the atrial and ventricular pulse generators 112 and 114 in a demand fashion in response to the absence or presence of cardiac activity in the appropriate chambers of the heart. The sensing circuits 138 and 140 receive control signals from the microcontroller 110 over signal lines 142 and 144 to control, for example, the gain and/or threshold of polarization charge removal circuitry (not shown) and the timing of blocking circuitry (not shown) optionally coupled to the inputs of the sensing circuits 138, 140.

Cardiac signals are supplied to an analog-to-digital (A/D) data acquisition system 146, which is configured to acquire intracardiac electrogram signals, convert the raw analog data into a digital signal, and store the digital signals for later processing and/or telemetric transmission to an external device 148. The data acquisition system 146 is coupled to the right atrial lead 16, the coronary sinus lead 14, the right ventricular lead 18 and the atrial lead system 20 through the switch 116 to sample cardiac signals across any pair of desired electrodes.

The data acquisition system 146 is coupled to the microcontroller 110, or other detection circuitry, to assist in detecting an evoked response from the heart 12 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 110 detects a depolarization signal during a window following a stimulation pulse, the presence of which indicates that capture has occurred. The microcontroller 110 enables capture detection by triggering the ventricular pulse generator 114 to generate a stimulation pulse, starting a capture detection window using the timing control circuitry 124 within the microcontroller 110, and enabling the data acquisition system 146 via control signal 150 to sample the cardiac signal that falls in the capture detection window and, based on the amplitude, determines if capture has occurred.

The microcontroller 110 is further coupled to a memory 152 by a suitable data/address bus 154. The programmable operating parameters used by the microcontroller 110 are stored in memory 152 and used to customize the operation of the exemplary stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

The operating parameters of the exemplary stimulation device 10 may be non-invasively programmed into the memory 152 through a telemetry circuit 156 in telemetric communication via communication link 158 with the external device 148, such as a programmer, local transceiver, or a diagnostic system analyzer. The microcontroller 110 can activate the telemetry circuit 156 with a control signal 160. The telemetry circuit 156 allows intracardiac electrograms and status information relating to the operation of the exemplary stimulation device 10 (as contained in the microcontroller 110 or memory 152) to be sent to the external device 148 through an established communication link 158.

The physiological sensors 132 referred to above can further include, for example, "rate-responsive" sensors that adjust pacing stimulation rates according to the exercise state of the patient. Accordingly, the microcontroller 110 responds by adjusting the various pacing parameters (such as rate, AV Delay, V-V Delay, etc.) at which the atrial and ventricular pulse generators 112 and 114 generate stimulation pulses.

The physiological sensors 132 may include mechanisms and sensors to detect bodily movement 134, minute ventilation 136, changes in blood pressure, changes in cardiac output, changes in the physiological condition of the heart, diurnal changes in activity (e.g., detecting sleep and wake states), G-force acceleration of the ICD case 200, duration of the cardiac QT interval, blood oxygen saturation, blood pH, changes in temperature, respiration rate, and QRS wave duration. While shown as being included within the exemplary stimulation device 10, the physiological sensor(s) 132 may also be external to the exemplary stimulation device, yet still be implanted within or carried by the patient, e.g., a blood pressure probe. Examples of physiological sensors external to the case 80 that may be deployed by stimulation device 10 include sensors that, for example, sense respiration activities, O2 saturation, evoked response, pH of blood, and so forth.

The illustrated physiological sensors 132 include one or more activity/position sensors 134 (e.g., 1D or 3D accelerometers, movement sensors, etc.) to detect changes in the patient's position. The activity/position sensors 134 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 136 may also be included in the physiological sensors 132 in order to sense rate and depth of breathing. Minute ventilation can be measured as the total volume of air that moves in and out of a patient's lungs in a minute. The MV sensor 136 may use an impedance measuring circuit 162 to sense air movement by measuring impedance across the chest cavity.

The impedance measuring circuit 162 is enabled by the microcontroller 110 via a control signal 164 and can be used for many things besides the abovementioned detection of air movement in and out of the lungs, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 162 may be coupled to the switch 116 so that any desired electrode may be used.

The exemplary stimulation device 10 additionally includes a battery 164 that provides operating power to all of the components shown in FIG. 2. The battery 164 is capable of operating at low current drains for long periods of time, e.g., less than 10 μA, and is capable of providing high-current pulses for capacitor charging when the patient requires a shock pulse (e.g., in excess of 2 A, at voltages above 2 V, for periods of 10 seconds or more). The battery 164 also desirably has predictable discharge characteristics so that elective replacement time can be detected. As one example, the exemplary stimulation device 10 employs lithium/silver vanadium oxide batteries.

The exemplary stimulation device 10 can further include magnet detection circuitry (not shown), coupled to the microcontroller 110, to detect when a magnet is placed over the exemplary stimulation device. A magnet may be used by a clinician to perform various test functions of the exemplary stimulation device 10 and/or to signal the microcontroller 110 that an external programmer 148 is in place to receive or transmit data to the microcontroller through the telemetry circuits 156.

The microcontroller 110 further controls a shocking circuit 166 via a control signal 168. The shocking circuit 166 generates shocking pulses of low (e.g., up to 0.5 joules), moderate (e.g., 0.5-10 joules), or high energy (e.g., 11-40 joules), as selected by the microcontroller 110. Such shocking pulses are applied to the patient's heart 12 through at least two shocking electrodes selected, for example, from the left atrial coil electrode 122, the RV coil electrode 132, and/or the SVC coil electrode 134. As noted above, the case 80 may act as an active electrode in combination with the RV coil electrode 132, or as part of a split electrical vector using the SVC coil electrode 134 or the left atrial coil electrode 122 (i.e., using the RV coil electrode 132 as a common electrode).

Cardioversion shocks are generally considered to be of low to moderate energy level so as to minimize pain felt by the patient, and/or synchronized with an R-wave and pertain to the treatment of tachycardia. Defibrillation shocks are generally of moderate to high energy level, corresponding to thresholds in the range of 5-40 joules, delivered asynchronously (since R-waves may be too disorganized), and pertain exclusively to the treatment of fibrillation. Accordingly, the microcontroller 110 is capable of controlling the synchronous or asynchronous delivery of the shocking pulses.

Figure 3:
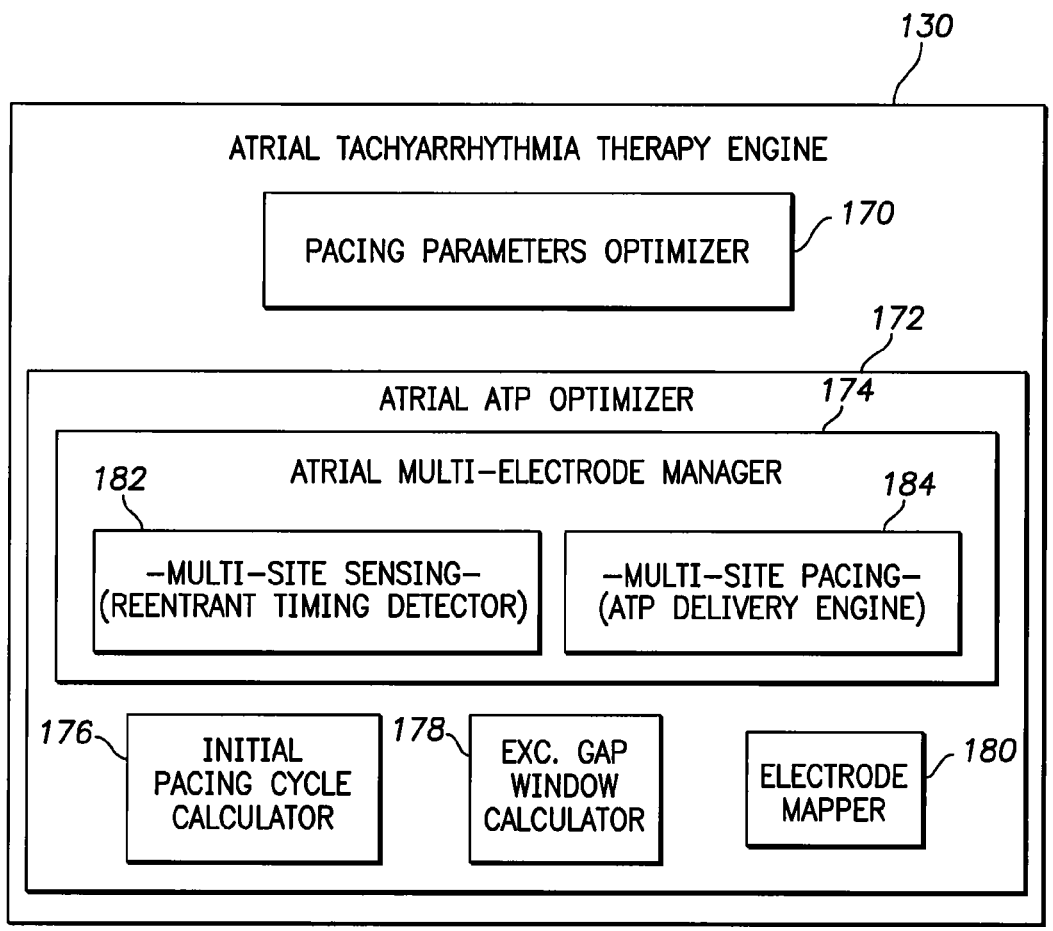
FIG. 3 is a functional block diagram of an atrial tachyarrhythmia therapy engine.

With reference to FIG. 3, the atrial tachycardia therapy engine 130 portion of the microcontroller 110 (FIG. 2) includes a pacing parameters optimizer 170 and an atrial ATP optimizer 172. In general, the atrial optimizer 172 provides pacing techniques to increase the efficacy of atrial tachyarrhythmias termination using the atrial electrodes 48. By analyzing atrial activation patterns during atrial tachyarrhythmia from electrograms of each electrode 48 site, the atrial optimizer 172 can determine the presence of a reentrant circuit and if such a circuit is present, which predefined or formed atrial electrodes set(s) 70 would produce the desired activation wave through the reentrant circuit. The atrial optimizer 172 may also determine ATP timing parameters.

The pacing parameters optimizer 170 works with the atrial optimizer 172 to compute the more ancillary pacing parameters to be used during ATP. The pacing parameters optimizer 170 can determine the number of the pacing stimuli to apply, the pulse width, the various time intervals between the pacing stimuli, etc. Typically, the pacing duration, the pacing threshold, the pacing rate; as well as the pulse width, the pulse shape, and the pulse interval optimize ATP parameters to minimize discomfort to patients, power consumption of the device, and also to reduce proarrhythmic effects of pacing. Thus, the optimal number of stimuli and typically a relatively lower pacing threshold will be selected as a part of the optimization process. The atrial tachyarrhythmia therapy engine 130 then uses all the parameters to deliver ATP in a manner that efficiently terminates atrial tachyarrhythmia.

The atrial optimizer 172 includes an atrial multi-electrode manager 174, an initial pacing cycle calculator 176, an excitable gap window calculator 178 and an electrode mapper 180. The atrial multi-electrode manager 174 portion of the atrial optimizer 172 includes a sensing division 182 and an ATP delivery division 184.

The sensing division or reentrant detector 182 detects the presence of a reentrant circuit in relation to electrode sites based on atrial activation patterns. Using the multiple electrodes implanted relative the atria, each electrode becomes a site for listening for the regular, relatively high frequency cycling of a reentrant circuit, or the tachyarrhythmic conduction being propagated from such a circuit. If only one reentrant circuit is active, then each electrode may sense a slightly different amplitude of the cyclical conduction and at a slightly different time, depending on distance of a particular electrode from the physical position of the reentrant circuit. If more than one reentrant circuit is active, then different electrodes may sense different frequencies and amplitudes of cycling. Details on one possible reentrant circuit or driver location process are included in U.S. patent application Ser. No. 11/458,655, filed Jul. 19, 2006, titled "System and Related Methods for Identifying a Fibrillation Driver", the disclosure of which is hereby incorporated by reference.

If the presence of a reentrant circuit has been detected by the reentrant detector 182, the atrial electrode mapper 180 identifies the positions of the atrial electrodes 48 with respect to the reentrant circuit based on the respective timings of signals sensed at each respective electrode. Using this temporal data and known positioning of the electrodes 48 with respect to each other, the electrode mapper 180 identifies one or more predefined multi-site electrode sets 70 capable of providing the desired activation wave front, or two or more individual electrodes that form a multi-site electrode set capable of providing the desired activation wave front.

In one implementation, ATP is applied one multi-site electrode set at a time, beginning at the electrode set that will deliver the desired activation wave front, which is closest to the reentrant circuit. If ATP applied at this electrode set fails to terminate the atrial tachyarrhythmia, then the multi-electrode manager 174 progresses to the next closest electrode set capable of delivering the desired activation wave front, and so on.

If atrial tachyarrhythmia persists, then ATP may be delivered using multiple multi-site electrode sets. In on such implementation, the ATP delivery engine 184 applies each pulse of the ATP in a syncopated manner across multiple multi-site electrode sets, so that each ATP pulse is sequentially applied in synchronization with the excitable gap as it passes each electrode in turn.

If the syncopated application of ATP just described fails to end the atrial tachyarrhythmia, then as a next option the ATP delivery engine 184 applies ATP simultaneously at multiple selected multi-site electrode sets or at all the available multi-site electrode sets, perhaps as a last option for ATP treatment of atrial tachyarrhythmia. Thus, the atrial optimizer 172 can apply a hierarchical protocol of increasingly invasive ATP applications.

Figure 4:
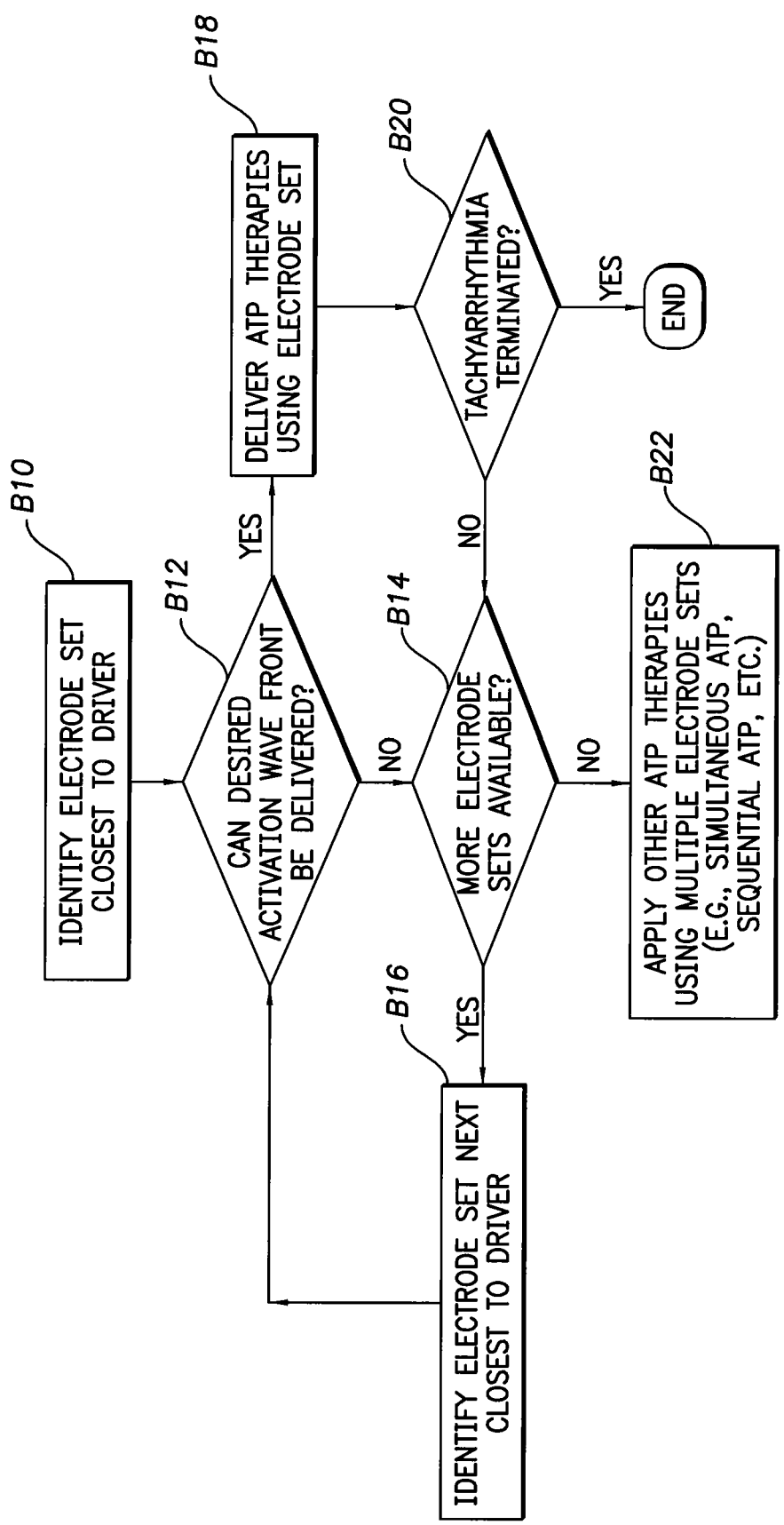
FIG. 4 is a process chart related to the application of ATP using predefined electrode sets selected from a number of available sets.

With reference to FIG. 4, an exemplary process for applying ATP using predefined multi-site electrode sets 70 includes several operations summarized in individual blocks. Some operations may be performed in hardware and/or as machine-readable instructions (software or firmware) that can be executed by a processor, such as microcontroller 110. The exemplary process may be implemented in connection with many suitably configured stimulation devices, although it will be described as being executed by the exemplary atrial tachyarrhythmia therapy engine 130 of the exemplary stimulation device 10.

Figure 5:
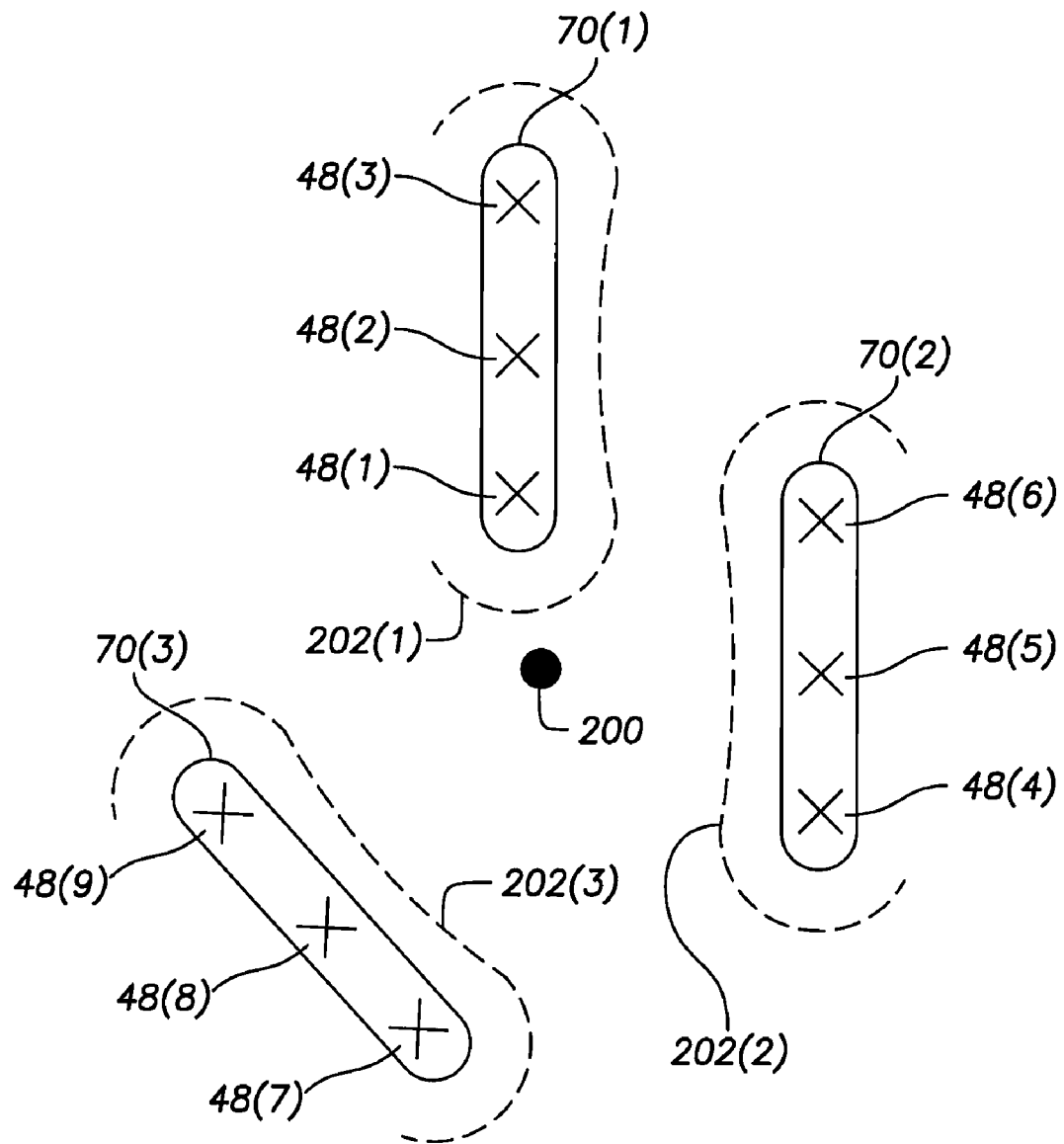
FIG. 5 is a schematic of various predefined electrode sets relative to a reentrant circuit or driver.

At block B10, the multi-site electrode set that is located closest to the reentrant circuit or driver is identified. With reference to FIG. 5, such a determination may be made based on the respective timing and/or magnitude of the signals sensed at the electrodes 48 in the electrode sets 70. For example, given first, second and third triple-site electrode sets 70(1), 70(2), 70(3), the first electrode set would be identified as closest to the driver 200 based on the position of electrode 48(1)—it is the closest electrode to the driver.

Continuing with FIG. 4, at block B12, a determination is made as to whether the identified, closest multi-site electrode set is positioned relative to the driver so as to deliver the desired activation wave front. Returning to FIG. 5, such a determination may be made based on the timing and/or magnitude of sensed signals at each of the electrodes 48 in the electrode set 70. With respect to the first electrode set 70(1), signals from the driver would reach the first electrode 48(1) before the second and third electrodes 48(2), 48(3); while reaching the second electrode 48(2) before the third electrode 48(3). From this timing data, and the known linear arrangement of the predefined triple-site electrode set, it may be determined that the positioning of the first electrode set 70(1) relative to the driver 200 is not conducive to producing the desired wave front. That is, the activation pattern 202(1) produced by ATP pulses applied through the first electrode set 70(1) would not result in a substantially linear to concave wave front passing through the driver 200. To the contrary, the wave front 202(1) toward the driver 200 that is produced by the first electrode set 70(1) would be convex, as if emanating from a single electrode 48(1).

Returning to FIG. 4, if it is determined that the identified electrode set will not produce the desired activation wave front, then at block B14 it is determined if more multi-set electrode sets are available for ATP consideration. If more sets are available, then at block B16, the multi-site electrode set that is located next closest to the reentrant circuit or driver is identified. The process then returns to block B12 to determine if this identified electrode set will produce the desired activation wave front.

Returning to the example of FIG. 5, triple-site electrode set 70(2) would be identified as the next closest electrode set based on the position of electrode 48(5). The sensing of signals from the reentrant circuit at each of the three electrodes 48(4), 48(5), 48(6) would occur at substantially the same time. Given this timing data, and the known linear arrangement of the predefined triple-site electrode sets, it may be determined that the second electrode set 70(2) could produce the desired activation wave front. That is, the activation pattern 202(2) produced by applying ATP pacing pulses through the second electrode set 70(2) would result in a substantially linear to concave wave front passing through the driver 200.

For ease in illustration, the activation patterns 202 shown in FIG. 5 are presented in idealized form, wherein the portion of the wave front directed toward the driver 200 is smooth, curvilinear and concave. In practice, however, it is understood that the wave fronts produced by multi-site electrode sets will most likely be characterized by undulating, non-smooth patterns which, while not as ideal as those shown in FIG. 5, are considered desirable. Such patterns are shown and described in the previously cited Ryu et al. article, which is hereby incorporated by reference.

Returning to FIG. 4, once a multi-site electrode set capable of delivering the desired activation wave front is identified, the process, at block B18, delivers ATP through the identified electrode set. Details related to the ATP therapy are described below. At block B20, a determination is made as to whether atrial tachyarrhythmia has been terminated by the applied ATP. If the tachyarrhythmia has terminated, the process ends. If, however, tachyarrhythmia persists, the process proceeds to block B14 where a determination is made regarding the presence of additional multi-site electrode sets that have not yet been considered for ATP. If additional electrode sets are present, the process proceeds to block B16 where the multi-site electrode set that is located next closest to the reentrant circuit or driver, and that has not yet been considered for ATP is identified. Continuing with the example of FIG. 5, the third electrode set 70(3) represents such an additional electrode set.

If at block B14, it is determined that additional multi-site electrode sets are not present, the process proceeds to block B22, where other ATP therapies may be applied using the present multi-site electrode sets. For example, as a first type of other therapy, ATP may be applied through each of the previously identified multi-site electrode sets simultaneously, sequentially or in a syncopated manner, as described below. As another or additional type of therapy, ATP may be applied simultaneously, sequentially or in a syncopated manner through all multi-site electrode set, regardless of the type of activation wave front it produces with respect to the driver.

As previously mentioned, instead of being grouped into predefined, multi-site electrode sets, the atrial electrodes 48 may be independently selectable to form multi-site electrode sets. For example, with reference to FIG. 1B, the atrial electrodes 48 in the regions of the pulmonary veins 62 may be arranged in a 3×4 array of individually selectable electrodes instead of the shown set of three, triple-site electrode sets.

Figure 6:
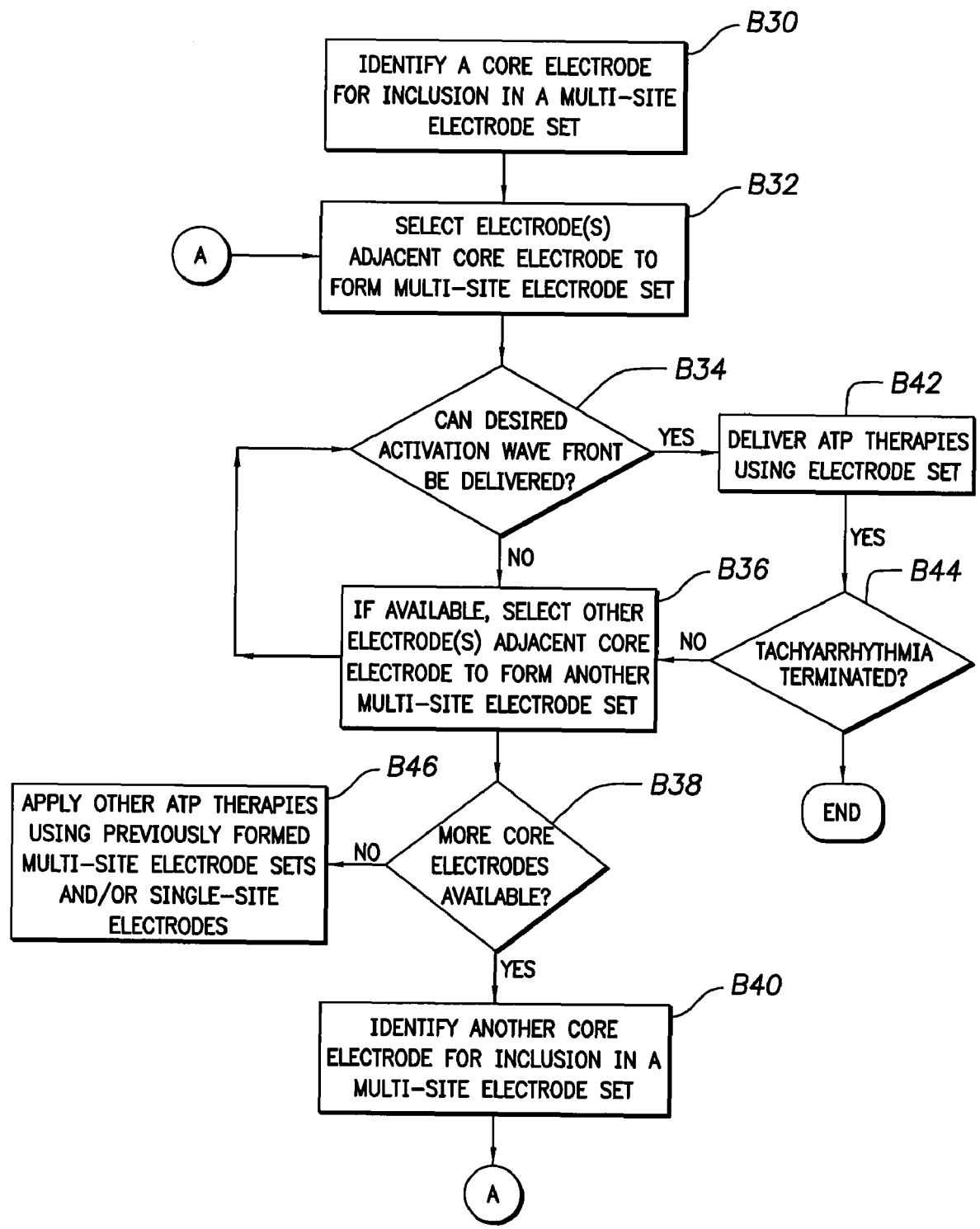
FIG. 6 is a process chart related to the application of ATP using electrode sets formed from a number of available electrodes.
Figure 7:
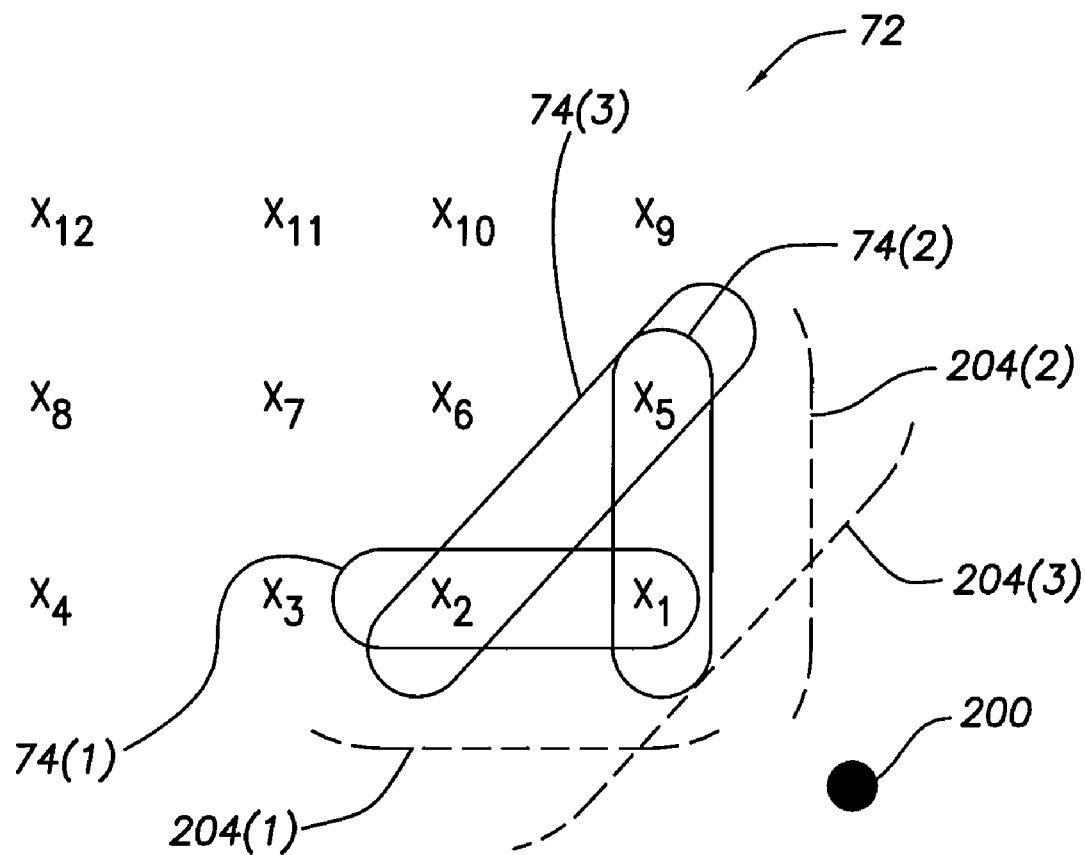
FIG. 7 is a schematic of possible electrode sets formed from an array of electrodes relative to a reentrant circuit or driver.

With reference to FIG. 6, an exemplary process for forming one or more multi-site electrode sets from a plurality of available electrodes includes, at block B30, identifying a core atrial electrode. Any electrode may be selected as a core electrode based on some type of criteria. For example, a core-electrode selection criterion may be based on distance from the driver 200, with the electrode closest to the driver being selected first. With reference to FIG. 7, such a determination may be made based on the respective timing and/or magnitude of the signals sensed at the electrodes in the electrode array 72. For example, given a 3×4 electrode array positioned relative to a driver 200, electrode $X_1$ would be identified as closest to the driver.

Returning to FIG. 6, at block B32, one or more additional electrodes adjacent the identified electrode, are selected as a possible electrode for a multi-site electrode set. For example, with reference to FIG. 7, electrodes adjacent $X_1$ would include one or both of $X_2$ and $X_5$.

Continuing with FIG. 6, at block B34, a determination is made as to whether the formed multi-site electrode set is positioned relative to the driver so as to deliver the desired activation wave front. Returning to FIG. 7, such a determination may be made based on the timing and/or magnitude of sensed signals at each of the electrodes in the formed electrode set. For example, if $X_2$ was selected, thus forming a dual-site electrode set consisting of electrodes $X_1$ and $X_2$, signals from the driver 200 would reach the first electrode $X_1$ before the second electrode $X_2$. From this timing data, and the known arrangement of the electrodes in the electrode array 72, it may be determined that the electrode set 74(1) formed from electrodes $X_1$ and $X_2$ is not conducive to producing the desired wave front. That is, the activation pattern 204(1) produced by ATP pulses applied through the first formed electrode set 74(1) would not result in a substantially linear to concave wave front passing through the driver 200.

If it is determined that the formed electrode set will not produce the desired activation wave front, the process proceeds to block B36 where, if available, another electrode adjacent the identified core electrode is selected to form another electrode set. For example, as shown FIG. 7, electrode $X_5$ is another electrode that is adjacent $X_1$. The process then returns to B34 where it is determined if the electrode set 74(2) formed by electrodes $X_1$ and $X_5$ electrode set will produce the desired activation wave front. In this example, like the electrode set 74(1) formed by electrodes $X_1$ and $X_2$, the wave front 204(2) produced by the electrode set 74(2) formed of electrodes $X_1$ and $X_5$ will not likely produce the desired wave front.

If there are no other electrodes adjacent the identified core electrode, the process proceeds to block B38 where it is determined whether more core electrodes are available. If another core electrode is available, the process proceeds to block B40 where a new core electrode is selected. For example, if the first core electrode was selected based on being closest to the driver, the next core electrode may be selected based on being next closest to the driver. In the example array of FIG. 7, a possible next core electrode is electrode $X_2$. Once the next core electrode is selected the process returns to block B32 where one or more adjacent electrodes are selected to form an electrode set with the current core electrode and further processing occurs as previously described.

With reference to FIG. 7, one possible adjacent electrode for $X_2$ is electrode $X_5$. The activation wave front 204(3) produced by this dual-site electrode set 74(3) would likely be substantially linear to slightly concave. As with previously described FIG. 5, for ease in illustration, the activation patterns 204 shown in FIG. 7 are presented in idealized form, wherein the portion of the wave front directed toward the driver 200 is smooth and linear or flat. In practice, however, it is understood that the wave fronts produced by multi-site electrode sets will most likely be characterized by undulating, non-smooth/linear/flat wave front patterns which, while not as ideal as those shown in FIG. 7, are considered desirable.

Returning to FIG. 6, once an electrode set capable of delivering the desired activation wave front is identified, the process, at block B42, delivers ATP through the formed multi-site electrode set. Details related to the ATP therapy are described below. At block B44, a determination is made as to whether atrial tachyarrhythmia has been terminated by the applied ATP. If the tachyarrhythmia has terminated, the process ends. If, however, tachyarrhythmia persists, the process proceeds to block B36 where processing proceeds as previously described.

If tachyarrhythmia persists, and all possible multi-site electrode sets have been formed with the current core electrode, and no more core electrodes are available, the process proceeds to block B46, where other ATP therapies may be applied using one or more of the previously formed multi-site electrode sets. For example, as a first type of other therapy, ATP may be applied through each of the previously formed multi-site electrode sets simultaneously, sequentially or in a syncopated manner, as described below. As other or additional types of therapy, ATP may be applied simultaneously, sequentially or in a syncopated manner through all multi-site electrode sets, regardless of the type of activation wave front it produces with respect to the driver. As still another therapy, ATP may be applied through all of the individual, single-site electrodes simultaneously, sequentially or in a syncopated manner.

The pacing of individual electrodes within a multi-site electrode set may be time controlled in order to produce the desired activation wave front from a group of electrodes that may not otherwise produce the desired wave front. For example, returning to FIG. 7, a triple-site electrode set may be formed from electrodes $X_1$, $X_2$ and $X_5$. Simultaneous application of pacing stimuli to the electrodes would likely produce a convex activation wave front which is not a desired wave front. If, however, pacing among the electrodes is timed so that pulses are delivered through adjacent electrodes $X_2$ and $X_5$ slightly prior to the pulses delivered through the core electrode $X_1$, the resulting wave front would likely be substantially linear to concave. The offset timing of the pacing pulses would most likely correspond to the offset timing noted during signal sensing at the respective electrodes in the set.

Returning to FIG. 3 and with respect to the application of ATP through a single multi-site electrode set (e.g. FIG. 4, block B18 and FIG. 5, block B42), once an electrode set has been selected or formed for ATP delivery, the atrial optimizer 172 and the pacing parameters optimizer 170 calculate the timing and other pulse characteristic and delivery parameters.

Regarding the timing of ATP, the reentrant detector 182 of the multi-electrode manager 174 senses the cycle duration of reentrant circuits, and more particularly senses the timing of the excitable gap segment of the reentrant circuit, at the multi-site electrode set. The excitable gap window calculator 178 then finds an excitable gap that can be stimulated to stop an atrial tachyarrhythmia. In one implementation, once the reentrant detector 182 finds the initial reentrant circuit cycle duration, e.g., by sensing intracellular upstroke potentials, then the window calculator 178 waits 80-90% of cycle, which typically is the starting point of the window. The voltage required can be high, e.g., at a current of 20 mA, 7.5-10 volts may be applied for approximately 0.5 ms.

The reentrant detector 182 searches for periodic signals at high rates, e.g., 105-107 millisecond cycles (around 10 Hertz), at extremely regular intervals. Unlike regular arrhythmia, these are not typically areas of tachyarrhythmia conduction, but instead are areas, i.e., "sites," where a driver exists. ATP is then applied by the ATP delivery engine 184 through the multi-site electrode set, at the cycle duration or frequency.

In one implementation, if atrial tachyarrhythmia persists, the ATP delivery engine 184 calculates a shorter cycle (i.e., a higher frequency) at which to apply ATP in subsequent attempts. For example, subsequent rounds of ATP may be applied at 95%, 90%, 85%, etc., of the initially sensed cycle duration. Relatively large stimuli are used, e.g., up to 100 volts. Thus, if the initial cycle duration is 100 ms or 99 ms, then subsequent bursts of ATP might be given at 95 ms, then 90 ms, then 85 ms, etc. In one implementation, multiple pulses of ATP are applied five times through the multi-site electrode set at each cycle duration or frequency. If the atrial tachyarrhythmia stops, then the next ATP cycle is not applied. In variations, the cycle duration of the applied ATP is decreased by the ATP delivery engine 184 in 5%, 3%, 2%, 1% intervals. Again, high voltage may be used if the tissue is not very excitable.

Regarding the application of ATP through multiple multi-set electrode sets (e.g. FIG. 4, block B22 and FIG. 6, block B46) the ATP delivery engine 184 paces simultaneously at each of the multi-site electrode sets, at a homogenous refractory period. Simultaneous stimulation may resynchronize the heart from the spontaneous conduction patterns of atrial tachyarrhythmias. Applying ATP at multiple multi-site electrode sets at once enables resynchronization of the atrium so that refractory periods are homogenized and less likely to have reentrant arrhythmia spontaneously occur. As refractory periods shrink, the tissue becomes more susceptible to faster reentrant cycles, but if this is controlled by the ATP delivery engine 184 the refractory periods lengthen, and the longer they are, the less likely spontaneous reentry will reoccur, because a larger circuit will be required.

The ATP delivery engine 184 may administer a simultaneous pulse at all multi-site electrode sets at once, delivered at very precise timing during the excitable gap. In one implementation, the precise timing is achieved merely by beginning stimulation timing at the high end of the excitable gap and changing the timing by increments until the low end of the excitable gap is stimulated. Sometime during this range of different timings, the midpoint of the excitable gap is approximated, offering assurance that the excitable gap has been stimulated directly, or "squarely."

In another implementation the ATP delivery engine 184 applies the ATP in a syncopated manner, with the cycle durations of the applied ATP pulses individualized for each multi-site electrode set, to coincide with the excitable gap as sensed by the respective multi-site electrode set. Thus, while one multi-site electrode set may be applying ATP at 10 ms intervals, another multi-site electrode set may be applying ATP at 92 ms intervals. Application of ATP at each multi-site electrode set is synchronized with the cycle duration, as sensed at by one or more of the electrodes in the respective electrode set.

It will be apparent from the foregoing that while particular forms of the invention have been illustrated and described, various modifications can be made without departing from the spirit and scope of the invention. For example, predefined electrode sets or individual electrodes placed in, on or around the ventricles may be used to apply multi-site-electrode-set ATP to terminate ventricular arrhythmias. Consequently, the specific structural and functional details disclosed herein are merely representative and do not limit the scope of the invention. The scope of the invention should be ascertained with reference to the claims.

What is claimed is:

1. A method of treating atrial tachyarrhythmia having an associated reentrant circuit, using one or more of a plurality of predefined, multi-site electrode sets implanted in or on the atria, each multi-site electrode set comprising at least two electrodes configured to have pacing stimuli applied thereto, said method comprising:
    selecting a plurality of electrode sets from the plurality of predefined, multi-site electrode sets;
    for each selected electrode set, sensing signals from the reentrant circuit at each electrode within the electrode set, determining whether the signals sensed at each electrode within the electrode set are sensed at approximately the same time; if the signals are sensed at approximately the same time, identifying the electrode set as an electrode set that will generate an electrical activation pattern through the reentrant circuit having a wave front between substantially flat and concave;
    based on the respective timing of the sensed signals for each selected electrode set, determining the relative closeness of the selected electrode sets to the reentrant circuit;
    identifying the electrode set closest to the reentrant circuit that is identified as an electrode set that will generate an electrical activation pattern through the reentrant circuit having a wave front between substantially flat and concave; and
    applying individual pacing stimuli to each of the at least two electrodes within the identified electrode set.

2. The method of claim 1 further comprising, if atrial tachyarrhythmia is still present;
    identifying the electrode set next closest to the reentrant circuit that is identified as an electrode set that will generate an electrical activation pattern through the reentrant circuit having a wave front between substantially flat and concave;
    applying individual pacing stimuli to each of the at least two electrodes within the identified electrode set.

3. The method of claim 2 wherein, if atrial tachyarrhythmia is still present, repeating the applying of pacing stimuli in the order of closeness of electrode sets to the reentrant circuit.

4. The method of claim 1 wherein a plurality of the electrode set are identified as an electrode set that will generate an electrical activation pattern through the reentrant circuit having a wave front between substantially flat and concave, and further comprising:
    in addition to the pacing stimuli being applied to the identified electrode set, applying pacing stimuli to the at least two electrodes of at least one additional electrode set selected from the plurality of the electrode sets that will generate an electrical activation pattern through the reentrant circuit having a wave front between substantially flat and concave.

5. The method of claim 4 wherein the pacing stimuli is applied to the at least one additional electrode set in one of a simultaneous, sequential or syncopated manner relative to the identified electrode set.

6. The method of claim 1 wherein applying pacing stimuli comprises applying stimuli to each of the at least two electrodes in an electrode set substantially simultaneously.

7. The method of claim 1 wherein applying pacing stimuli comprises applying stimuli to each of the at least two electrodes in an electrode set in an offset manner corresponding to an offset in the timing of signals sensed at the electrodes.

8. A system for treating atrial tachyarrhythmia having an associated reentrant circuit, said system comprising:
    a plurality of predefined, multi-site electrode sets adapted to be positioned on, in or around the atria, each multi-site electrode set comprising at least two electrodes configured to have pacing stimuli applied thereto;
    a pulse generator connected to the multi-site electrode sets; and
    a processor operative to:
        select a plurality of electrode sets from the plurality of predefined, multi-site electrode sets;
        for each selected electrode set, sense signals from the reentrant circuit at each electrode within the electrode set, determine whether the signals sensed at each electrode within the electrode set are sensed at approximately the same time; if the signals are sensed at approximately the same time, identify the electrode set as an electrode set that will generate an electrical activation pattern through the reentrant circuit having a wave front between substantially flat and concave;
        based on the respective timing of the sensed signals for each selected electrode set, determine the relative closeness of the selected electrode sets to the reentrant circuit;
        identify the electrode set closest to the reentrant circuit that is identified as an electrode set that will generate an electrical activation pattern through the reentrant circuit having a wave front between substantially flat and concave;

cause the pulse generator to apply individual pacing stimuli to each of the at least two electrodes within the identified electrode set.

9. The system of claim 8 wherein at least some of the electrode sets are adapted to be positioned on the atria relative to the epicardial surface.

10. The system of claim 8 wherein at least some of the electrode sets are adapted to be positioned in the atria relative to the endocardial surface.

11. The system of claim 8 wherein the electrode sets are adapted to be positioned near one or more of Bachmann's bundle, the interatrial septum, the posterior region of the right atrium, the high right atrium, the right atrial free wall along the crista terminalis, the coronary sinus, the low right atrial free wall, inside the pulmonary veins, around the pulmonary veins, the posterior-inferior region of the left atrial free wall, along the ligament of Marshall, the junctional area of the left atrial appendage and the left pulmonary veins.

12. The system of claim 8 further comprising a sensor for receiving signals from the plurality of electrode sets, wherein the processor is further operative to detect atrial tachyarrhythmia based on signals from the electrode sets.

* * * * *